US00PP32610P2

(12) United States Plant Patent
Hendricus Oudolf

(10) Patent No.: US PP32,610 P2
(45) Date of Patent: Dec. 8, 2020

(54) ***MOLINIA* PLANT NAMED 'WHIRLWIND'**

(50) Latin Name: *Molinia caerulea*
Varietal Denomination: Whirlwind

(71) Applicant: Future Plants Licentie B.V., Lisserbroek (NL)

(72) Inventor: Petrus Hendricus Oudolf, Hummelo (NL)

(73) Assignee: FUTURE PLANTS LICENTIE B.V., Lisserbroek (NL)

( * ) Notice: Subject to any disclaimer, the term of this patent is extended or adjusted under 35 U.S.C. 154(b) by 0 days.

(21) Appl. No.: 16/873,294

(22) Filed: Mar. 11, 2020

(51) Int. Cl.
*A01H 5/12* (2018.01)
*A01H 5/02* (2018.01)

(52) U.S. Cl.
USPC ..... Plt./384

(58) Field of Classification Search
USPC ..... Plt./384
CPC ..... A01H 5/12; A01H 5/02; A01H 6/00
See application file for complete search history.

*Primary Examiner* — Keith O. Robinson
(74) *Attorney, Agent, or Firm* — Penny J. Aguirre

(57) ABSTRACT

A new cultivar of *Molinia* plant named 'Whirlwind' that is characterized by its plant size of 1.35 m in height and width, its elegant and rather open inflorescences that are light brown in color, its stem that remain upright and don't lodge until late fall, and its floriferous blooming habit.

2 Drawing Sheets

Botanical classification: *Molinia caerulea.*
Varietal denomination: 'Whirlwind'.

CROSS-REFERENCE TO A RELATED APPLICATION

This application is related to a European plant breeders' rights application filed on Mar. 4, 2017, application No. 2017/0693. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Molinia caerulea* and will be referred to hereafter by its cultivar name, 'Whirlwind'. 'Whirlwind' represents a new cultivar of herbaceous perennial, an ornamental grass grown for landscape use.

The new cultivar arose from open-pollination of an unnamed and unpatented proprietary plant of *Molinia caerulea* from the Inventor's breeding program in Hummelo, The Netherlands in early fall of 2011. The male parent is therefore unknown. The Inventor selected the new cultivar as unique in November of 2012 from the resulting seedlings.

Asexual propagation of the new cultivar was first accomplished by division in 2014 by the Inventor in Hummelo, The Netherlands. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Whirlwind' as a unique cultivar of *Molinia.*

1. 'Whirlwind' exhibits a plant size of 1.35 m in height and width.
2. 'Whirlwind' exhibits elegant and rather open inflorescences that are light brown in color.
3. 'Whirlwind' exhibits stem that remain upright and don't lodge until late fall.
4. 'Whirlwind' exhibits a floriferous blooming habit.

The female parent of 'Whirlwind' differs from 'Whirlwind' in having a shorter plant height, less conspicuous fall foliage coloration, and stems that lodge (collapse) considerably earlier in fall. 'Whirlwind' can be most closely compared to *Molinia caerulea* cultivars 'Moorflamme' (not patented) and 'Moorhexe' (not patented). 'Moorflamme' differs from 'Whirlwind' in having a much shorter plant height, inflorescences that are bristly, more stiff and lighter brown in color. 'Moorhexe' differs from 'Whirlwind' in having a shorter plant height, inflorescences that are bristly, more stiff and darker brown in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited to websites by Oudolf Garden Detroit (asking for donations for plants for future additions when available for a garden dedicated to the Inventor) and Visions (a photography company).

BRIEF DESCRIPTION OF THE DRAWINGS

The accompanying colored photographs illustrate the overall appearance and distinct characteristics of the new

*Molinia*. The photographs were taken of a 3-year-old plant of 'Whirlwind' as grown outdoors in a garden in Hummelo, The Netherlands.

Figure 1:
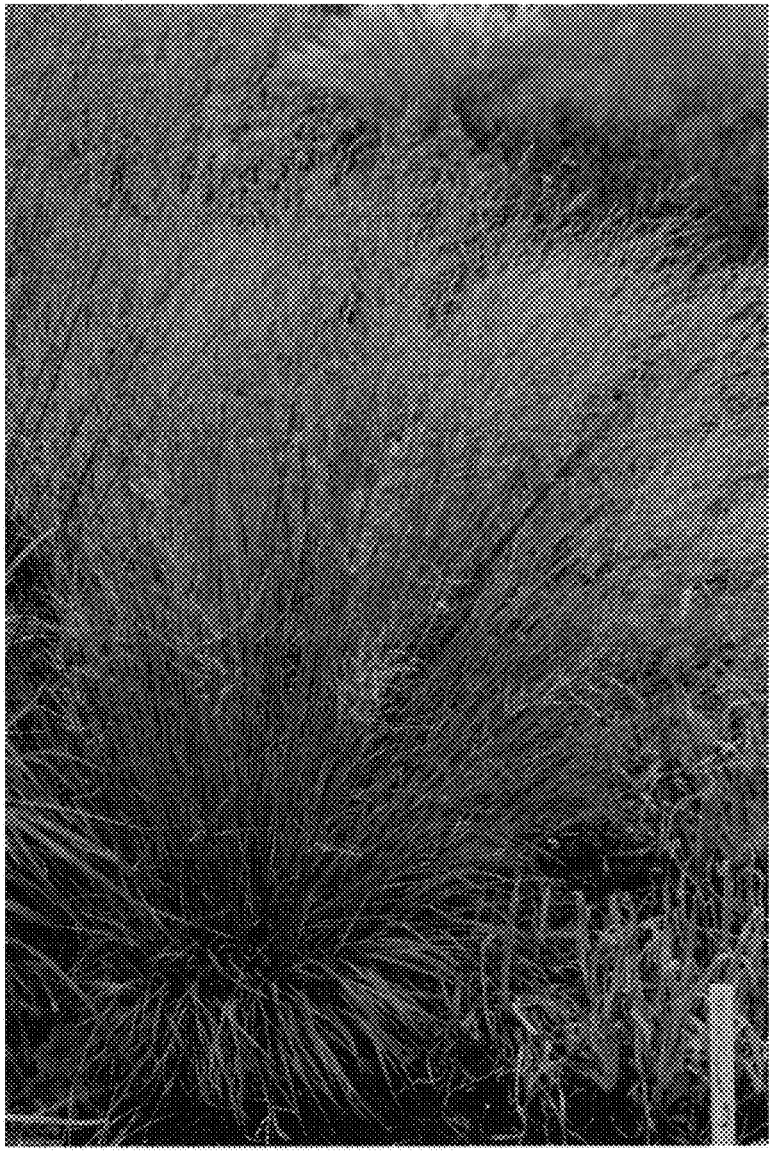

The photograph in FIG. 1 provides a side view of 'Whirlwind' in bloom.

Figure 2:
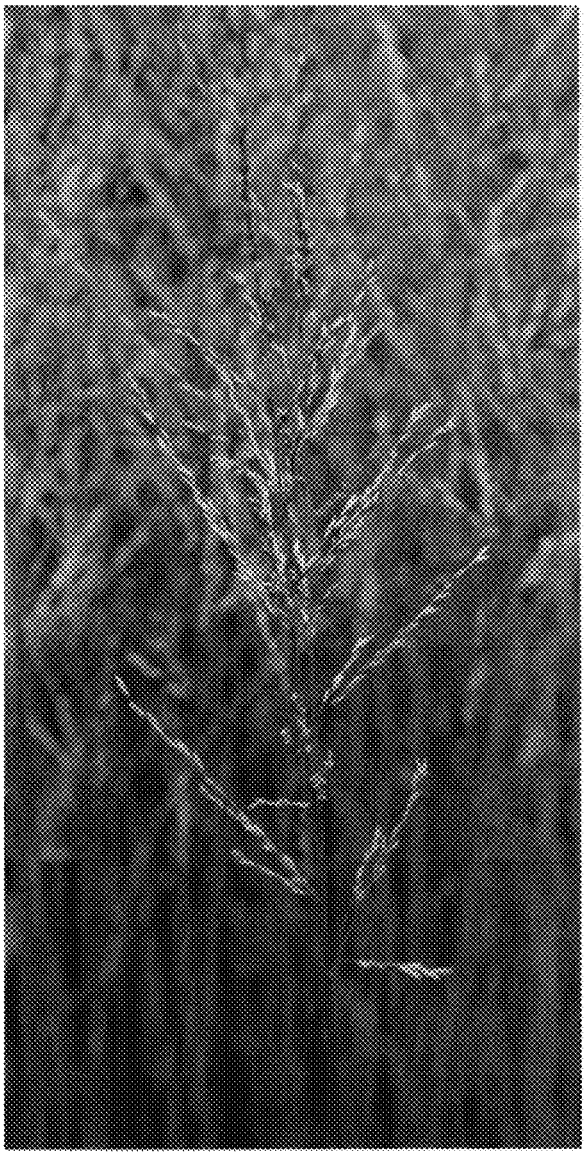

The photograph in FIG. 2 provides a close-up view of the inflorescences of 'Whirlwind'.

The colors in the photographs are as close as possible with the digital photography techniques available, the color values cited in the detailed botanical description accurately describe the colors of the new *Molinia*.

DETAILED BOTANICAL DESCRIPTION

The following is a detailed description of plants 3-years-in-age as field grown in Lisserbroek, The Netherlands. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Blooming period*.—Late summer into autumn in The Netherlands.

*Plant type*.—Herbaceous perennial grass.

*Plant habit*.—Obovate, broadly upright, formed by near globular basal rosettes of leaves with inflorescences carried well above the foliar plane.

*Height and spread*.—An average of 1.35 m in height and width as grown in the landscape.

*Cold hardiness*.—At least in U.S.D.A. Zone 4.

*Environmental stresses*.—Good tolerance to wind and rain.

*Diseases*.—No resistance or susceptibility to diseases has been observed.

*Root description*.—Dense, freely branching, medium thickness, slightly fleshy, 155D in color.

*Propagation*.—Division.

*Growth rate*.—Moderate.

*Root development*.—About 13 weeks to produce a young rooted plant from a division.

*Shoot description*.—About 250 basal shoots, unbranched.

Foliage description:

*Leaf shape*.—Linear, flat to slightly carinate.

*Leaf arrangement*.—Alternate.

*Leaf division*.—Simple.

*Leaf quantity*.—Average of 5 per shoot.

*Leaf margin*.—Entire.

*Leaf base*.—Decurrent.

*Leaf apex*.—Narrow and long acuminate.

*Leaf venation*.—Parallel, only main vein visible on under surface; 137A in color.

*Leaf width*.—An average of 6 mm in width, sheathed portion; 4 mm.

*Leaf length*.—An average of 33.7 cm (excluding decurrent base), sheathed portion; 20.9 cm.

*Leaf surface*.—Glabrous and smooth on both surfaces, ligule glabrous.

*Leaf color* (*both surfaces*).—Young and mature upper surface 137A, young and mature lower surface NN137B, both surfaces change to 164B in the fall.

Flower description:

*Inflorescence type*.—Airy panicle of racemes at terminus of stem, primarily symmetrical.

*Inflorescence size*.—An average of 30.1 cm in length and 6 cm in diameter.

*Flower quantity*.—Average of 250 per inflorescence, 50,000 per plant.

*Flower buds*.—Average of 3 mm in length, 1 mm in diameter, linear in shape, surface is smooth, glabrous and slightly glossy, 161C in color.

*Spikelet description*.—Consisting of 2 glumes and 2 lemmas, upright, moderately free habit, no fragrance, 3.5 mm in height, 1.5 cm in diameter, 1.5 cm in length, lasts an average of 1 month, persistent, surface is glabrous and slightly glossy, glumes; 2 glumes oppositely placed at the base of each spikelet, lemmas oppositely placed above the glumes, slightly concave, linear in shape, average of 3.5 mm in length, 1 mm in width, narrow acute tip, cuneate base, 161C in color, lemmas; moderately concave, linear in shape, average of 3 mm in length, 1 mm in width, narrowly acute tip, cuneate base, 161C in color.

*Peduncles*.—Average of 91.2 cm in length, 1.25 mm in diameter, held in a 20° angle to vertical, strong, smooth, glabrous and moderately glossy surface, 138B in color and changing to 144B in color at the base.

*Pedicels*.—Average of 4 mm in length, 0.4 mm in diameter, held in a 5° angle to peduncle, strong, smooth, glabrous and matte surface, 162B to 162C in color.

Reproductive organs:

*Androecium*.—Stamens; 3, anthers; 2 mm in length and 0.3 mm in width, 162C in color, filament; 155A in color, 1.5 mm in length, pollen; none observed.

*Gynoecium*.—Pistil; 2, 2 mm in length, stigma; feather-like, 1 mm in length, 0.4 mm in diameter, 84B to 84C in color, style; 1 mm in length, 153A in color, ovary; 162C in color.

*Seed*.—None observed to date.

It is claimed:

1. A new and distinct cultivar of *Molinia* plant named 'Whirlwind' as herein illustrated and described.

* * * * *